United States Patent [19]

Oertle et al.

[11] 4,092,844
[45] June 6, 1978

[54] HYDROGEN PROBE WITH LIMITED ACTIVE AREA

[75] Inventors: Donald H. Oertle; Richard M. Vennett; Burton M. Casad; Fred J. Radd, all of Ponca City, Okla.

[73] Assignee: Continental Oil Company, Ponca City, Okla.

[21] Appl. No.: 716,321

[22] Filed: Aug. 20, 1976

[51] Int. Cl.² .................... G01N 27/46; G01N 27/62; G01N 7/10
[52] U.S. Cl. .................... 73/23; 204/195 R; 204/195 P; 324/33; 73/19
[58] Field of Search ............... 204/1 T, 195 R, 195 P, 204/129; 324/33; 73/19.23

[56] References Cited

U.S. PATENT DOCUMENTS

| 2,749,293 | 6/1956 | Wahlin | 204/129 |
| 3,357,903 | 12/1967 | Lawrence | 204/1 T |
| 3,565,769 | 2/1971 | Holden et al. | 204/195 R |
| 3,835,013 | 9/1974 | Grubb et al. | 204/195 P |
| 3,886,444 | 5/1975 | Roy et al. | 73/19 |
| 3,942,546 | 3/1976 | Radd | 73/23 |

OTHER PUBLICATIONS

Norton, "J. of Applied Physics," vol. 11, Apr. 1940, pp. 262, 265–267.

Primary Examiner—T. Tung
Attorney, Agent, or Firm—Richard W. Collins

[57] ABSTRACT

An insertion-type hydrogen probe with a defined active length is described. The probe is formed of a thin-walled, hydrogen-permeable material, and a hydrogen-impermeable liner inside the probe blocks out all but the defined active section of the probe. The interior of the probe is subjected to high vacuum, and the hydrogen permeation through the active portion of the probe is determined, for example, by the current output of an ion pump used with the probe. To prevent bimetallic cell interface effects, the probe is constructed so that only a single metal is exposed to the primary environment being studied.

4 Claims, 2 Drawing Figures

HYDROGEN PROBE WITH LIMITED ACTIVE AREA

BACKGROUND OF THE INVENTION

1. Field of the Invention

This invention relates to hydrogen-permeable probes for exposure to environments that form atomic hydrogen. The probe is normally connected to a pressure-indicating or other quantitative gas sensing device such as an ion pump. More particularly, the invention relates to hydrogen probes having a limited active area such that the active part of the probe can be positioned in a desired area of a container.

2. Brief Description of the Prior Art

The use of hydrogen-permeable probe members in conjunction with an electronic pump means for determining the amount of hydrogen permeating the probe as an indication of the corrosive activity of a hydrogen-forming environment is well known.

U.S. Pat. Nos. 3,498,900 and 3,942,546 disclose the combination of a hydrogen-permeable probe and an ion pump which provides a current reading corresponding to the amount of dissociated hydrogen permeating the hydrogen-permeable section of the probe. Those patents further disclose details regarding suitable probe materials and associated apparatus for use in conjunction with the probe and ion pump combination. The probes described in those patents include finger probes and patch probes of various materials and configurations.

A particular hydrogen probe for use in sodium-cooled nuclear reactors is described in U.S. Pat. No. 3,886,444. The probe described in that patent has a thin layer of refractory metal coated on the inner wall surface of the probe for controlling the rate of permeation of hydrogen through the tube.

Attempts have been made in the past to combine a limited active area probe section with a non-permeable section, but the resulting cell effect of the bimetallic couple in an electrolyte made this undesirable. It has also been proposed to use a limited active area probe electrically insulated from the remainder of the probe structure, but the electrical insulation gave sealing and strength problems. It has further been attempted to mask off a portion of a probe with a non-metallic coating. This has the disadvantage that the coatings can be easily damaged in use, and can be chemically deteriorated in corrosive environments.

SUMMARY OF THE INVENTION

According to the present invention, an insertable hydrogen probe having a limited active area is provided. The entire exterior of the probe that will be exposed to a corrosive environment is made of a single metal such as carbon steel such that no bimetallic couple is produced. A hydrogen-impermeable sleeve is attached to the interior of the probe along a portion of its length, such that only the hydrogen which permeates the unlined portion of the probe is measured by the ion pump or other gas-determining device utilized with the probe.

It is accordingly an object of this invention to provide a probe having a limited active area positionable at a selected location within a container.

It is a further object to provide such a probe which does not form a bimetallic couple when placed in an electrolyte within a container.

DESCRIPTION OF THE PREFERRED EMBODIMENT

Figure 1:
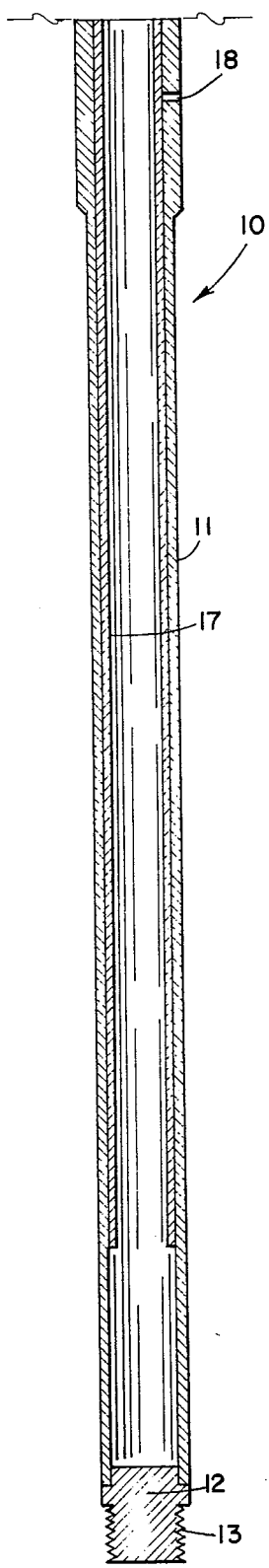
FIG. 1 is a cross-sectional view of a probe in accordance with the invention.

The most preferred embodiment of the invention will now be described by reference to the drawings.

A probe device shown generally at 10 includes an elongated tubular member 11 open at one end and formed of a hydrogen-permeable material. Carbon steel tubing or pipe is a convenient material for forming this member, particularly for low or moderate temperature use, and particularly suitable materials are three-eighths inch steel tubing or one-quarter inch Schedule 80 carbon steel pipe. An end plug 12 also formed of carbon steel is shown welded to one end of the tubular member 11, and the end plug 12 includes external thread means 13 for purposes to be explained later. It is essential that the end plug 12 be of the same material as the tubular member 11 in order to avoid the formation of a bimetallic couple when the probe is placed in a corrosive liquid environment.

An inner sleeve or liner 17 is positioned within tubular member 11 and each end thereof is sealingly joined to tubular member 11 such that hydrogen permeating through tubular member 11 along the length lined by sleeve 17 does not have access to the ion pump. Sleeve 17 may be formed of stainless steel or any other material which is impermeable to hydrogen at the intended conditions of use. Stainless steel is particularly suitable for applications at temperatures below 250° C, although at temperatures higher than 250° C stainless steel begins to become permeable to hydrogen, such that other known materials should be used for high temperature situations.

When the tubular member 11 is carbon steel and the sleeve 17 is stainless steel, it is particularly preferable to seal the end furthest from the ion pump by silver soldering or other low temperature process to avoid formation of a heat-affected zone in the tubular member, which could produce a bimetallic couple. The seal between tubular member 11 and sleeve 17 at the end nearest the ion pump can be formed by brazing, welding or other suitable methods.

A vent 18 is provided through tubular member 11 to prevent a pressure build-up between the interior of the lined portion of tubular member 11 and the exterior of sleeve 17. The vent may be covered with adhesive tape, plastic tubing or other suitable means to keep moisture out of the annulus between sleeve 17 and tubular member 11, and hydrogen can easily escape through the tape or tubing.

Figure 2:
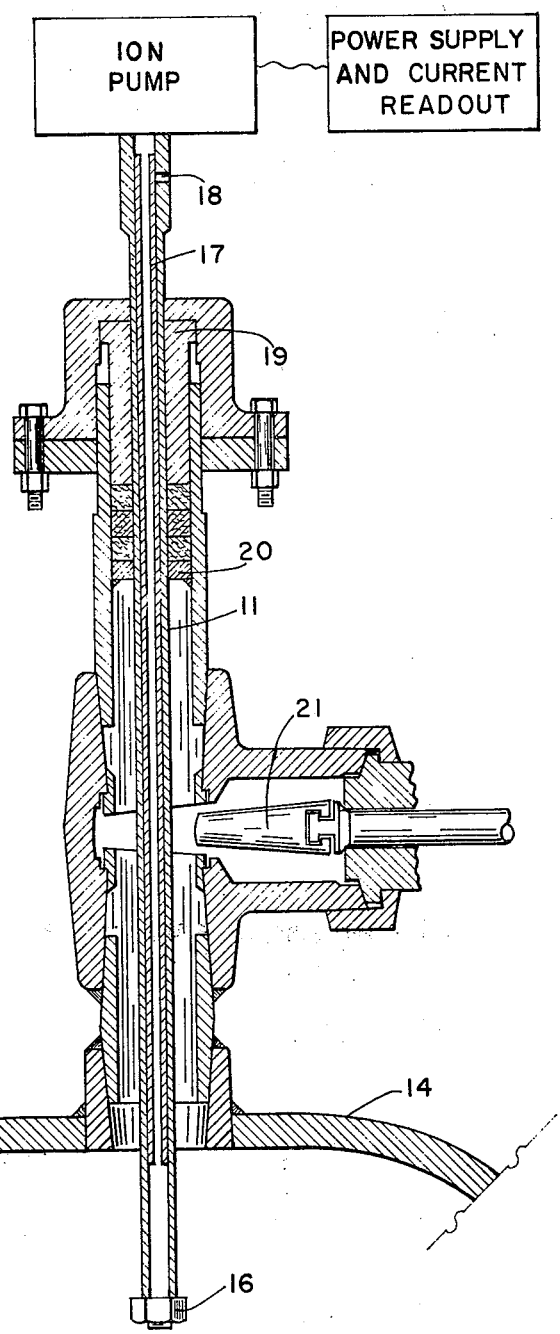
FIG. 2 is a view, partly in cross-section, showing the probe of the invention attached to a vessel.

The active length of the probe is the portion extending beyond the end of sleeve 17, and this may be any fraction of the entire length of the probe depending upon the particular use and environment for which it is to be used. As shown in FIG. 2, the active section extends into vessel 14, and the lined portion extends through a valve attached to vessel 14 so that only the corrosion activity occurring within vessel 14 is measured, and any corrosion occurring within the valve body, which might not be representative of conditions in vessel 14, does not contribute to the reading obtained or the ion pump current readout.

A nut 16 is shown in FIG. 2 threaded to the threads 13 on the end plug 12 on tubular member 11. The purpose of this nut 16 is to enable an operator to safely remove the probe from the vessel. The procedure for removing the probe includes sliding it outwardly through packing gland 19 until nut 16 contacts stop member 20. The probe cannot be completely removed until the packing gland is disassembled, but since nut 16 has contacted stop member 20, the operator can close valve gate 21 to isolate packing gland 19 from the interior of vessel 14 without any danger of valve gate 21 having failed to close due to contact with tubular member 11.

It will be appreciated that the specific configuration and the size of the probe can vary depending upon the use to which it is to be put. Also, the materials of construction may be other than as described, so long as at the conditions of use the tubular member 11 is formed of a hydrogen-permeable material, and the sleeve 17 is formed of a hydrogen-impermeable material. It is also essential that the portion of the probe exposed to an environment to be tested be of the same material throughout so that a bimetallic couple will not be formed. The gas-sensing device utilized with the probe need not be an ion pump but could be any other sensitive gas-detecting device. The invention is also useful for detection of gases other than hydrogen, in which case tubular member 11 should be formed of a material permeable to the particular gas being determined, and sleeve 17 should be formed of a material impermeable to the specific gas being determined.

Numerous variations and modifications of the embodiment shown and described will be apparent to those skilled in the art, and the true scope of the invention includes such embodiments as are defined by the appended claims.

We claim:
1. A hydrogen probe device comprising:
an elongated tubular member formed of a hydrogen-permeable metallic material, said member having a first closed end formed of said hydrogen-permeable metallic material and a second open end for connection to a hydrogen-sensing device;
an inner liner in said tubular member, said liner being formed of a hydrogen-impermeable material and extending a part of the length of said tubular member and being sealingly joined at each end to the interior of said tubular member whereby hydrogen permeating the portion of the length thereof between the sealed ends of said liner is prevented from entering the interior of said probe and passing out the open end thereof; and a
vent means through the wall of said tubular member between the ends of said liner whereby hydrogen which permeates said tubular member between the sealed ends of said liner may pass freely from between the outer surface of said liner and the lined inner surface of said tubular member thereby preventing a buildup of pressure between the interior of the lined portion of said tubular member and the exterior of said liner, the extent of said vent means being from the exterior to the interior of said tubular member.

2. The hydrogen proble device of claim 1 wherein said elongated tubular member is formed of carbon steel.

3. The hydrogen probe device of claim 1 wherein said liner is formed of stainless steel.

4. The hydrogen probe device of claim 1 wherein the first closed end is formed of a plug welded to said tubular member, said plug having an exterior threaded extension.

* * * * *